(12) United States Patent
Ludwig

(10) Patent No.: US 6,410,723 B1
(45) Date of Patent: Jun. 25, 2002

(54) VDUP1 PROMOTER AND METHODS OF USE THEREOF

(75) Inventor: Dale Ludwig, Rockaway, NJ (US)

(73) Assignee: Imclone Systems Incorporated, New York, NY (US)

( * ) Notice: Subject to any disclaimer, the term of this patent is extended or adjusted under 35 U.S.C. 154(b) by 0 days.

(21) Appl. No.: 09/625,040

(22) Filed: Jul. 24, 2000

(51) Int. Cl.⁷ .......................... C07H 21/04; C12N 5/00; C12N 5/02
(52) U.S. Cl. .................. 536/24.1; 536/23.1; 435/320.1; 435/325
(58) Field of Search ................ 536/23.1, 24.1; 435/320.1, 325, 366, 365

(56) References Cited

PUBLICATIONS

Young, et al., Alteration of Gene Expression in Rat Mammary Tumors Induced by N–Methyl–N–nitrosourea (1996), Molecular Carcinogenesis, vol 15, pp. 251–260.

Nishiyama, et al., Identification of Thioredoxin–binding Protein–2/Vitamin $D_3$ Up–regulated Protein 1 as a Negative Regulator of Thioredoxin Function and Expression (1999), The Journal of Biological Chemistry, vol 274(31), pp. 21645–21650.

Chen, et al., Isolation and characterization of a novel cDNA from HL–60 cells treated with 1,25–dihydroxyvitamin D–3 (1994), Biochimica et Biophysica Acta, vol. 1219, pp. 26–32.

Yang, et al., Expression of a vitamin D–regulated gene (VDUP–1) in untreated– and MNU–treated rat mammary tissue (1998), Breast Cancer Research and Treatment, vol 48, pp. 33–44.

Primary Examiner—Remy Yucel
Assistant Examiner—Konstantina Katcheres
(74) Attorney, Agent, or Firm—Kenyon & Kenyon

(57) ABSTRACT

A substantially purified nucleic acid molecule comprising a VDUP1 promoter region, capable of directing expression of a polypeptide encoding sequence to which it is operably linked, whose expression is induced to maximal levels as a result of prolonged cell culture.

25 Claims, 6 Drawing Sheets

Mouse VDUP1 Promoter Sequence

```
CAAAGCCACACACCCAAATAACCCAGCTCCCCAAGAGAGTCCCCTGATGAGGTTCAGCGTCCCCGGGTCCCACGCTCCCGGGGGAGGGAGGCCACCCGT
                                                                            |_____|
                                                                                Sp1                    520

CGCCCCCGGGCCCCGGCCCCTCCTCCTGGCAAGGCTGCCCACCCGAACAACAACCATTTTCCCCGCTAGGAGCACCCGTGTCCAAGCGGCCCCGGGGCCTC
   |_____|
          Sp1                                                                                          420

CCAAT box       USF/MLTFrepeat
                              |_____|       |_____|
GCTGATTGGTTGGAGGCCTGCTAAACAAGGGCCAAGTACGCCAATGGGAGAACTGTCCACGAGCGCCTCCAGGCCAGCACTCGCCGTGGAGCG
                                                           →                                         320

TATA box                                c-Rel/NF-Kap
              |_____|                                |_____|
CCAAGGCCAGCGGCCTATATAAGCCCGTTTCCCGCAGCCCTTGACACTCTCCTCCTCGGTCTGGGGTTTCCAGAGTTTCTCCAGTTGAGGTTGACAGCT
                  Start →                                                                             220

GTTATTTTCTCCTGAAACGCTTTTTGGCACAGCCCAGGCACCTTTTGGAAAAGTGTTAGGGTTTGTTTGAACTTTCTTTACAT
                                                                                                      120

TTTCGTTTGGGTTTCAAGCCCTGACTTTACGGAGGCGAGCTCTCTTCGTTTGCTTGCTTTGAAGGGTTCTTAAAGATTTTTTCCTCTCCGGCTTTCGTTTTTCT
       Start →                                                                                          20

TGAACCCCACTCGGCTCAATC
           →
           ATG
```

FIG.3

SEQUENCE LISTING

<160> NUMBER OF SEQ ID NOS: 4

<210> SEQ ID NO 1
<211> LENGTH: 1448
<212> TYPE: DNA
<213> ORGANISM: Murine sp.

<400> SEQUENCE: 1

```
ctctagtcag ctcctgaggc atctctcagc aaggtttgcc agataactaa g tgaaactaa      60 cacagctcca gcgccggtga aattgaaaca ggttagggac atgcatttca t ttagtgaat     120 ttggagagag gacagagggg ggaaaagaat gacaggaact cgaaaacaaa g taaggagtg    180 aggttctttt tcttcctttt tctttctttc ttttattta ttttttttggt t tgtccacct    240 cttgtttcct ggagaaacaa ggacggggga gccatcagtg tgaaagtaaa c acctcacaa    300 agctgcagtg aggaacaagg gaacatatac aaaatgttcc ccaacttcac a ggtacactg    360 aagagatgag gggataagca acaggatgtg gacactccct tactgcttcc g ctccagaga    420 acagaataga atgtaatggg cgaggaacag tagcagcaca tagggcatg a aatgagggg    480 gaaatgaggg gaacccacca gagcattcac cagaaaggac tgaaagccag a ctttaaaat   540 atctgacaag ttctcgtctg gagagaccgc agccttttat tcttcaatag a agtgcaata   600 ggagcatatc gggtgggctc tttctcacta acacgactgc actctcgccc t ccgctccat   660 cctggagtat cctcggtgcg atgggattgt ttttcacaag acttgcgaac t tgtgagcca  720 ggaataaatg gtcacctcga aatgaattgc gctggctcag gcgagtcatg a aatcctctc  780 ctaagcacat ttttctttca cctaaaaaaa gaaggggggaa aaaaaaaca a agcacacac  840 ccaaataacc cagctcccaa gaggagtccc ctggatgagg ttcagggtcc c ggggtccca  900
```

-continued

```
gcctcccggg gggagggagg gcacccgtcg ccccgggccc cgcccctcct g ctggcaagg      960 ctgcgcaccc gaacaacaac cattttcccc gctaggagca caccgtgtcc a cgcgccccg     1020 gcggcctcgc tgattggttg gaggcctggt aaacaagggc caagtagcca a tgggagaac     1080 tgtgcacgag ggctgcacga gcctccaggc cagcactcgc gtggagcgcc a agccaggcg     1140 gctatataag ccgtttccgg cagccgcttg acactctcct cctctggtct c gggtttcc     1200 agagtttctc cagttgcgga agacagctgt tattttctc ctgaaagctt t tggcacagc     1260 cggcaggctg aaacttccag gcaccttttg gaaaagttgt tagggtttgt t tgaagcttt    1320 ctttacattt tcgtttgggt tttcaagccc tgactttacg gaggcgagct c ttcgtttgc    1380 tttgaagggt tcttaaagat ttttttcctc tccggctttc gttttcttg a acccactcg    1440 gctcaatc                                                               1448
```

<210> SEQ ID NO 2
<211> LENGTH: 452
<212> TYPE: DNA
<213> ORGANISM: Murine sp.

<400> SEQUENCE: 2

```
agcacaccgt gtccacgcgc cccggcggcc tcgctgattg gttggaggcc t ggtaaacaa       60 gggccaagta gccaatggga gaactgtgca cgagggctgc acgagcctcc a ggccagcac      120 tcgcgtggag cgccaagcca ggcggctata agccgtttcc ggcagccgc t tgacactc       180 tcctcctctg gtctcggggt ttccagagtt tctccagttg cggaagacag c tgttatttt      240 tctcctgaaa gctttggcac agccggcag gctgaaactt ccaggcacct t ttggaaaag      300 ttgttagggt ttgtttgaag cttctcttac attttcgttt gggttttcaa g ccctgactt      360 tacggaggcg agctcttcgt ttgctttgaa gggttcttaa agatttttttt c ctctccggc     420 tttcgttttt cttgaaccca ctcggctcaa tc                                    452
```

<210> SEQ ID NO 3
<211> LENGTH: 597
<212> TYPE: DNA
<213> ORGANISM: Murine sp.

<400> SEQUENCE: 3

```
agctcccaag aggagtcccc tggatgaggt tcagggtccc ggggtccag c ctcccgggg       60 ggagggaggg cacccgtcgc cccgggcccc gcccctcctg ctggcaaggc t gcgcacccg     120 aacaacaacc attttcccg ctaggagcac accgtgtcca cgcgcccgg c ggcctcgct     180 gattggttgg aggcctggta acaagggcc aagtagccaa tgggagaact g tgcacgagg      240 gctgcacgag cctccaggcc agcactcgcg tggagcgcca agccaggcgg c tatataagc     300 cgtttccggc agccgcttga cactctcctc ctctggtctc ggggtttcca g agtttctcc    360 agttgcggaa gacagctgtt attttctcc tgaaagcttt tggcacagcc g gcaggctga    420 aacttccagg caccttttgg aaaagttgtt agggtttgtt tgaagctttc t ttacatttt    480 cgtttgggtt tcaagccct gactttacgg aggcgagctc ttcgtttgct t tgaagggtt    540 cttaaagatt ttttcctct ccggctttcg ttttcttga cccactcgg c tcaatc         597
```

<210> SEQ ID NO 4
<211> LENGTH: 1002
<212> TYPE: DNA
<213> ORGANISM: Murine sp.

```
<400> SEQUENCE: 4
acagtagcag cacatagggg catgaaatga gggggaaatg aggggaaccc a ccagagcat       60 tcaccagaaa ggactgaaag ccagacttta aaatatctga caagttctcg t ctggagaga      120 ccgcagcctt ttattcttca atagaagtgc aataggagca tatcgggtgg g ctctttctc      180 actaacacga ctgcactctc gccctccgct ccatcctgga gtatcctcgg t gcgatggga      240 ttgtttttca caagacttgc gaacttgtga gccaggaata aatggtcacc t cgaaatgaa      300 ttgcgctggc tcaggcgagt catgaaatcc tctcctaagc acatttttct t tcacctaaa      360 aaaagaaggg ggaaaaaaaa aacaaagcac acacccaaat aacccagctc c caagaggag      420 tcccctggat gaggttcagg gtcccggggt cccagcctcc cggggggagg g agggcaccc      480 gtcgcccggg gccccgcccc tcctgctggc aaggctgcgc acccgaacaa c aaccatttt      540 ccccgctagg agcacaccgt gtccacgcgc cccggcggcc tcgctgattg g ttggaggcc      600 tggtaaacaa gggccaagta gccaatggga gaactgtgca cgagggctgc a cgagcctcc      660 aggccagcac tcgcgtggag cgccaagcca ggcggctata taagccgttt c cggcagccg      720 cttgacactc tcctcctctg gtctcggggt ttccagagtt tctccagttg c ggaagacag      780 ctgttatttt tctcctgaaa gcttttggca cagccggcag gctgaaactt c caggcacct      840 tttggaaaag ttgttagggt ttgtttgaag ctttctttac attttcgttt g ggttttcaa      900 gccctgactt tacggaggcg agctcttcgt ttgctttgaa gggttcttaa a gatttttt       960 cctctccggc tttcgttttt cttgaaccca ctcggctcaa tc                         1002
```

VDUP1 PROMOTER AND METHODS OF USE THEREOF

BACKGROUND OF THE INVENTION

1. Field of the Invention

This invention relates to a novel promoter for gene expression and uses thereof. More particularly, this invention relates to nucleic acid sequences encoding a functional promoter for the VDUP1 gene that correspond in structure and/or properties to the native genomic form of this promoter, and the use of such nucleic acid sequences for heterologous nucleic acid sequence expression.

2. Background

The VDUP1 gene (designated for Vitamin D3 UP-regulated 1) was first described as a gene strongly induced by vitamin D3 in human HL-60 cells. See, e.g., Chen and DeLuca, Biochem. Biophys. Acta, 1219:26–32 (1994). The exposure of HL-60 cells to vitamin D3 leads to cell differentiation into monocytes or macrophages. In that study, VDUP1 was isolated from a cDNA library by differential hybridization of mRNA from cells treated or untreated with 1,25-dihydroxyvitamin D3. Induction of VDUP1 by vitamin D3 was shown to occur even in the presence of the protein synthesis inhibitor, cyclohexamide. Further, exposure to cyclohexamide alone could induce VDUP1 several fold. More recently, it has been determined that VDUP1 is down-regulated in rat tumors generated by N-methyl-N-nitrosurea induction. See e.g., Young, et al., Mol. Carcinog., 4:251–60 (1996); Yang, et al., Breast Cancer Res. Treat., 48:33–44 (1998). No correlation between these two modulatory effects on VDUP1 expression has been characterized. Clues to the biological function of the VDUP1 gene product were recently described in a paper by Nishiyama, et al. J. Biol. Chem., 274:21645–50(1999). Protein binding studies in the yeast two-hybrid system, identified the VDUP1 gene product as a protein that specifically binds to the disulfide reducing protein, thioredoxin (TRX). These provide evidence that VDUP1 protein may only bind to reduced TRX and perhaps inhibits its reducing potential. In addition, overexpression of VDUP1 inhibits the expression of TRX. In HL-60 cells treated with vitamin D3, the induction of VDUP1, in agreement with the results of Chen and DeLuca, Biochem. Biophys. Acta, 1219:26–32 (1994), correlates with a significant decrease in the expression of TRX. TRX over-expression has been correlated with growth promotion. The biological significance of this direct effect of VDUP1 on TRX expression and redox function may be to modulate oxidation-reduction regulation of cellular factors and processes involved in cell growth and differentiation.

Antibodies represent one of the best therapeutic candidates for the treatment of disease due to their inherent specificity for their target molecule. However, a major drawback to their effective clinical use is the fact that they are bio-molecules and must be synthesized by expression from transfected cells in culture or transgenic plants or animals. The same is true for any reactive bio-molecule, such as a growth factor or enzyme, that may have utility in research or clinical application. To date, the majority of bio-molecules now produced are generated from cultured cells. Systems have been developed to enhance the overall output of protein production from cells, including promoter selection, gene targeting, gene amplification, highly selective transfection markers, fluorescence activated cell sorting, and medium supplementation. Each of these have shown some degree of success in enhancing gene expression of the desired molecule. In regard to promoter selection, the majority of expression vectors used for this application employ viral promoters, such as cytomegalovirus (CMV) or SV40. The CMV promoter in particular is often utilized primarily due to its strong constitutive expression in a variety of cell types and its propensity for up-regulation by exogenous agents and cellular stress. During standard cell culture for the production of bio-molecules, expression of recombinant protein occurs in a fairly linear fashion throughout the culture period, typically 10–14 days. However, noticeable enhancement of production usually occurs in late culture. Typically, expression of the CMV promoter is also frequently down-regulated following stable integration into cellular genomes, despite exhibiting strong expression in transient transfection experiments (M. Stiaski, Gene Expression Systems, 211–233, (J. M Fernandez and J. P Hoeffler ed., Academic Press 1999)). Thus there is a need for a strong constitutive promoter whose regulation can be enhanced during all stages of prolonged cell culture and upon genomic integration.

SUMMARY OF THE INVENTION

This invention relates to a substantially purified nucleic acid molecule comprising a VDUP1 promoter region, whose expression is induced to maximal levels as a result of prolonged cell culture. This invention also relates to a nucleic acid molecule having a sequence consisting of: (a) a nucleic acid sequence substantially similar to that of SEQ ID NO:1, or a fragment thereof, which exhibits promoter activity; (b) a nucleic acid sequence substantially complementary to the nucleic acid sequence of (a) or an active fragment thereof; or (c) a nucleic acid sequence that hybridizes to the nucleic acid sequences of (a) or (b) or fragments thereof under high stringency conditions. In another aspect, the invention relates to expression vectors comprising the aforementioned nucleic acid sequences and host cells transformed with these expression vectors.

The invention also relates to methods for detecting test agents which modulate the expression of the VDUP1 promoter described above comprising contacting a host cell transformed with an expression vector comprising the VDUP1 promoter DNA sequence operably linked to a reporter nucleic acid sequence with the test agent and comparing the level of transcription of the reporter nucleic acid sequence product produced in the presence of the test agent to the level of transcription produced in its absence.

In one embodiment of this aspect of the invention there are provided methods of screening for test compounds or factors that modulate the activity of the VDUP1 promoter by: (a) contacting host cells transformed with a nucleic acid molecule containing the VDUP1 promoter disclosed herein operably linked to a reporter nucleic acid sequence with a test medium containing the test compound under conditions which allow for expression of the reporter nucleic acid sequence; (b) measuring the expression of the reporter nucleic acid sequence in the presence of the test medium; (c) contacting host cells with a control medium which does not contain the test compound but is otherwise identical to the test medium in (a), under conditions identical to those used in (a); (d) measuring the expression of reporter nucleic acid sequence in the presence of the control medium; and (e) correlating any difference in expression between (b) and (d) to the ability of the test compound to regulate the activity of the VDUP1 promoter.

The invention also relates to methods of expressing a heterologous nucleic acid sequence in a mammal comprising introducing into mammalian cells a vector comprising the nucleic acid sequence encoding a VDUP1 promoter operably linked to a nucleic acid sequence encoding a heterologous protein, polypeptide, hormone, ribozyme or antisense RNA, whereby the heterologous protein, polypeptide hormone, ribozyme or antisense RNA is expressed.

The invention also relates to transgenic or chimeric animals whose cells express a heterologous nucleic acid sequence under the transcriptional control of a VDUP1 promoter.

BRIEF DESCRIPTION OF THE DRAWINGS

FIG. 3 shows the 3' most 620 bases of the VDUP1 promoter indicating the two Sp1 sites, the CCAAT box, the USF/MLTF repeat, the TATA box, both start sites as well as the c-Rel/NF-κB site.

DETAILED DESCRIPTION OF THE INVENTION

Figure 1:
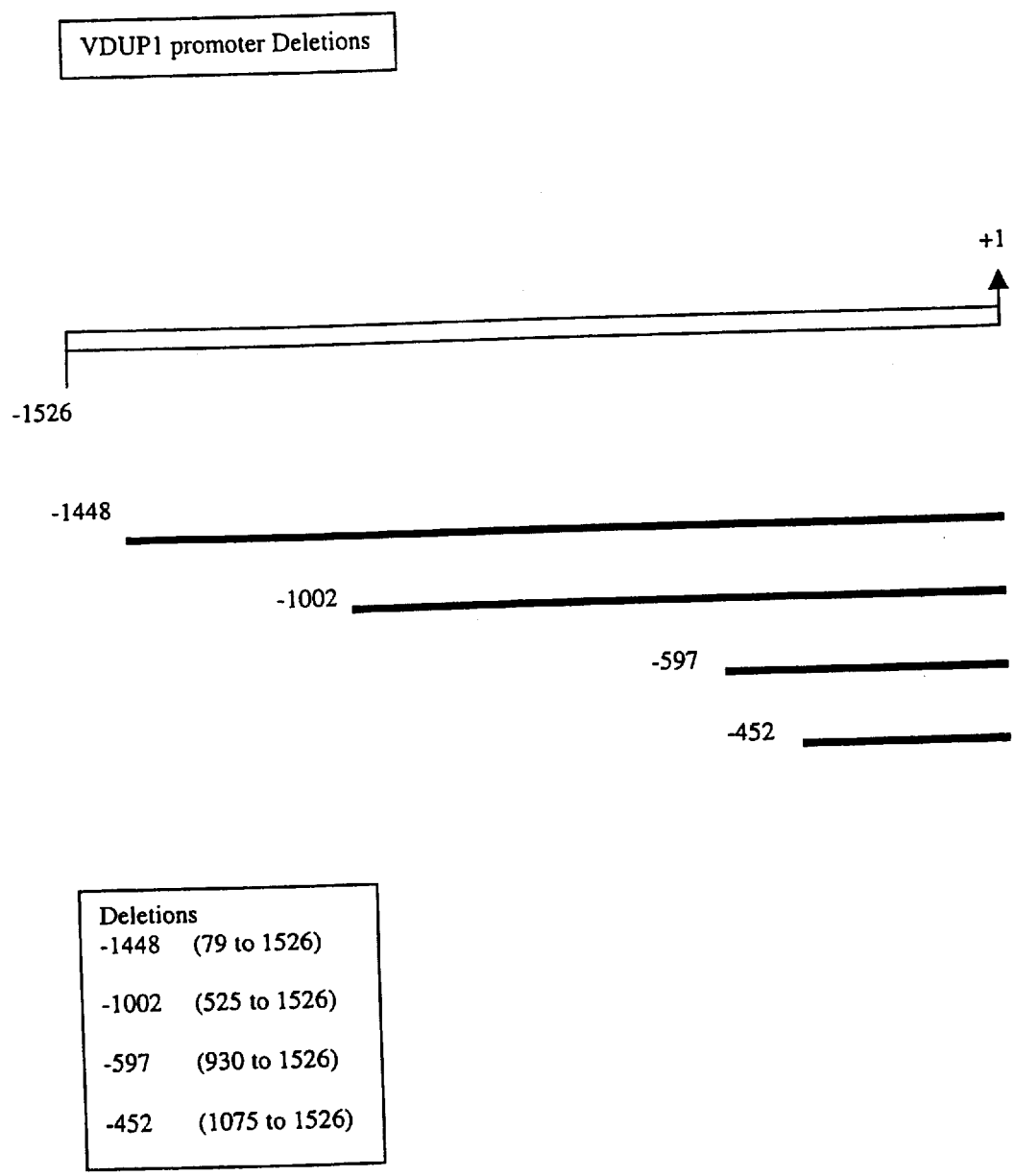
FIG. 1 is a schematic drawing of the VDUP1 promoter and deletion constructs thereof.

This invention relates to novel promoters for the VDUP1 gene, nucleic acid constructs comprising such promoters operatively linked to sequences encoding a nucleic acid sequence product, such as a protein, polypeptide, hormone, ribozyme, or antisense RNA, recombinant cells comprising such nucleic acid constructs, screening for therapeutic drugs using such cells. To this end, the responsible promoter elements effect high level inducible expression of heterologous nucleotide.

This invention further relates to a method of identifying factors or metabolites necessary for induction of high level nucleic acid sequence expression through the VDUP1 promoter, by manipulation of medium supplements and culture parameters.

Before describing the invention in greater detail the following definitions are set forth to illustrate and define the meaning and scope of the terms used to describe the invention herein:

The term "nucleic acid molecule" is meant to include DNA, RNA and mixed DNA-RNA sequences. In addition to the typically found A, T, U, G and C residues, a nucleic acid molecule may also include related residues such as, for example, inosine (I).

The term "promoter region" refers to a DNA sequence that functions to control the transcription of one or more nucleic acid sequences, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, calcium or cAMP responsive sites, and any other nucleotide sequences known to act directly or indirectly to regulate transcription from the promoter.

The term "promoter activity" refers to the extent of expression of nucleotide sequence that is operably linked to the promoter whose activity is being measured. Promoter activity may be measured directly by determining the amount of RNA transcript produced, for example by Northern blot analysis or indirectly by determining the amount of product coded for by the linked nucleic acid sequence, such as a reporter nucleic acid sequence linked to the promoter.

The term "substantially purified" refers to a nucleic acid sequence, polypeptide, protein or other compound which is essentially free, i.e., is more than about 50% free of, preferably more than about 70% free of, more preferably more than about 90% free of, the polynucleotides, proteins, polypeptides and other molecules that the nucleic acid, polypeptide, protein or other compound is naturally associated with.

The term "high stringency conditions" refers to conditions selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C. By using probes, particularly labeled probes of DNA sequences, one can isolate homologous or related genes. The source of homologous genes may be any species, e.g., primate species, particularly humans, rodents, such as rats and mice, canines, felines, bovines, ovines, equines, yeast, Drosophila, Caenhorabditis, etc.

The term "operably linked" refers to the linkage of a DNA segment to another DNA segment in such a way as to allow the segments to function in their intended manners. A DNA sequence encoding a gene product is operably linked to a regulatory sequence when it is ligated to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers may be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induction" refers to an increase in nucleic acid sequence transcription or expression brought about by a transcriptional inducer, relative to some basal level of transcription.

The term "repression" refers to a decrease in nucleic acid sequence transcription or expression brought about by a transcriptional repressor, relative to some basal level of transcription.

The term "heterologous DNA" or "heterologous RNA" refers to DNA or RNA that does not occur naturally as part of the genome or DNA or RNA sequence in which it is present, or that is found in a cell or location or locations in the genome or DNA or RNA sequence that differs from that which it is in found in nature. Heterologous DNA or RNA is not endogenous to the cell into which it is introduced, but has been obtained from another cell or synthetically or recombinantly produced. Generally, though not necessarily, such DNA encodes RNA and protein not normally produced by the cell in which the DNA is transcribed or expressed. Similarly exogenous RNA encodes protein not normally expressed in the cell in which the exogenous RNA is present. Heterologous DNA or RNA may also be referred to as foreign DNA or RNA. Any DNA or RNA that one of skill in the art would recognize as heterologous or foreign to the cell in which it is expressed is herein encompassed by the term heterologous DNA or heterologous RNA. Examples of heterologous DNA include, but are not limited to, DNA that encodes a protein, polypeptide, reporter nucleic acid sequence, transcriptional or translational regulatory sequences, selectable or traceable marker protein, such as a protein that confers drug resistance, RNA including mRNA and antisense RNA, and ribozymes. A preferred embodiment of the present invention relates to the VDUP1 promoter or sequences substantially similar thereto, operably linked to heterologous nucleic acid sequences encoding immunogloublin light and/or heavy chains.

A "reporter nucleic acid sequence" is a DNA molecule that expresses a detectable gene product, which may be RNA or protein. The detection may be accomplished by any method known to one of skill in the art. For example, detection of mRNA expression may be accomplished by using Northern blot analysis and detection of protein may be accomplished by staining with antibodies specific to the protein, e.g. Western blot analysis. Preferred reporter nucleic acid sequences are those that are readily detectable. A reporter nucleic acid sequence may be operably linked in a DNA construct with a regulatory DNA sequence such that detection of the reporter nucleic acid sequence product provides a measure of the transcriptional activity of the regulatory sequence. Examples of reporter nucleic acid sequences include, but are not limited to, those coding for alkaline phosphatase, chloramphenicol acetyl transferase (CAT), luciferase, beta-galactosidase and alkaline phosphatase.

The term "polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide.

The term "recombinant polynucleotide" as used herein refers to a polynucleotide of genomic, cDNA, semisynthetic or synthetic origin which, by virtue of its origin or manipulation: (1) is not associated with all or a portion of the polynucleotide with which it is associated in nature and/or (2) is linked to a polynucleotide other than that to which it is linked in nature. The term "cDNA" or "complementary DNA" refers to single stranded or double stranded DNA sequences obtained by reverse transcription of messenger RNA isolated from a donor cell. For example, treatment of messenger RNA with a reverse transcriptase such as AMV reverse transcriptase or M-MuLV reverse transcriptase in the presence of an oligonucleotide primer will furnish an RNA-DNA duplex which can be treated with RNase H, DNA polymerase and DNA ligase to generate double stranded cDNA. If desired, the double stranded cDNA can be denatured by conventional techniques such as shearing to generate single stranded cDNA.

An "expression vector" is any genetic element, e.g., a plasmid, chromosome, virus, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, bacteriophages and cosmids. Vectors may contain polynucleotide sequences which are necessary to effect ligation or insertion of the vector into a desired host cell and to effect the expression of the attached segment. Such sequences differ depending on the host organism; they include promoter sequences, such as the novel VDUP1 promoters of the present invention, to effect transcription, enhancer sequences to increase transcription, ribosomal binding site sequences and transcription and translation termination sequences. Alternatively, expression vectors may be capable of directly expressing nucleic acid sequence products encoded therein without ligation or integration of the vector into host cell DNA sequences.

The term "substantial homology" or "substantial similarity" in the nucleic acid context as used herein, means that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95–98% of the nucleotides. Alternatively, substantial homology or substantial similarity exists between two nucleic acid sequences when the sequences or their complementary strands will hybridize under highly stringent hybridization conditions to a template strand. Selective hybridization exists when the hybridization is more selective than total lack of specificity. See, Kanehisa, Nucleic Acids Res., 12:203–213 (1984). The nucleic acid sequences provided above can be used by those skilled in the art to practice the invention as disclosed herein without undue experimentation using, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

The term "substantially complementary" refers to probe or primer sequences which hybridize to the sequences provided under stringent conditions. Under stringent hybridization conditions, only highly complementary nucleic acid sequences hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The terms "transformed" or "transfected" are used interchangeably and refer to the process by which exogenous DNA or RNA is transferred or introduced into an appropriate host cell. Typically, the exogenous DNA will comprise the promoter regions of this invention, preferably the VDUP1 promoter, operably linked to a heterologous DNA sequence. Such transfected cells include stably transfected cells wherein the inserted DNA is rendered capable of replication in the host cell. Typically, stable transfection requires that the exogenous DNA be transferred along with a selectable marker nucleic acid sequence, such as for example, a nucleic acid sequence that confers antibiotic resistance, which enables the selection of the stable transfectants. This marker nucleic acid sequence may be ligated to the exogenous DNA or be provided independently by simultaneous cotransfection along with the exogenous DNA. Transfected cells also include transiently expressing cells that are capable of expressing the RNA or DNA for limited periods of time. The host cell maybe a prokaryotic or eukaryotic cell. The transfection procedure depends on the host cell being transfected. It can include packaging the polynucleotide in a virus as well as direct uptake of the polynucleotide. Transformation can result in incorporation of the inserted DNA into the genome of the host cell or the maintenance of the inserted DNA within the host cell in plasmid form. Methods of transformation/transfection are well known in the art and include, but are not limited to, direct injection, such as microinjection, viral infection, particularly replication-deficient adenovirus infection, electroporation, lipofection, calcium phosphate-mediated direct uptake and the like.

The term "transfer vector" refers to a plasmid that enables the integration of a recombinant nucleic acid sequence into virus DNA by homologous recombination.

The term "host cell" generally refers to prokaryotic or eukaryotic cells and includes any transformable cell which is capable of expressing a protein and can be, or has been, used as a recipient for expression vectors or other transfer DNA.

The term "recombinant cells" refers to cells that have been modified by the introduction of heterologous DNA or RNA.

COS cells and HL-60 cells, 293 cells, mouse myeloma SP2/0 cells, and NSO cells are preferred for introduction of heterologous DNA operably linked to the VDUP1 promoters of this invention, although almost any mouse or human production cell line could be used.

It is to be understood that this invention is intended to include other forms of expression vectors, host cells and transformation techniques which serve equivalent functions and which become known to the art hereto.

As noted above, the present invention relates to a recombinant nucleic acid molecule comprising the VDUP1 promoter region. This invention provides a nucleic acid molecule having a sequence comprising: (a) a nucleic acid sequence substantially similar to that of SEQ ID NO:1 or a fragment thereof, exhibiting promoter activity, in particular VDUP1 promoter activity; (b) a nucleic acid sequence substantially complementary to said nucleic acid sequence of (a), or an active fragment thereof; or (c) a nucleic acid sequence that hybridizes under stringent conditions to said nucleic acid sequences of (a) or (b) or fragments thereof. This invention also provides novel deletion constructs of the VDUP1 promoter, which alter promoter activity relative to that of the naturally occurring promoter.

The deletion constructs are obtained by progressively deleting 5' sequences from the VDUP1 promoter SEQ ID NO:1 sequence shown in FIG. 1. Those segments that have altered regulatory activity, include a 1002bp segment (FIG. 1; SEQ ID NO:4), the 597bp segment (FIG. 1; SEQ ID NO:3), and the 452bp segment (FIG. 1; SEQ ID NO:2), which includes minimal promoter sequences that provide VDUP1 activity.

Preferably, such nucleic acid molecules will be substantially similar to the nucleic acid sequence shown in SEQ ID NO:1. Alternatively, those skilled in the art can practice the invention by repeating the experimental procedures carried out by the inventors and described herein for the isolation and characterization of the VDUP1 promoters, their transfection into host cells, and high level induction of expression of heterologous DNA operably linked to said VDUP1 promoters.

When used to induce high levels of expression, the expression vectors of this invention can be used to express heterologous sequences in addition to reporter nucleic acid sequences such as alkaline phosphatase, luciferase, beta-galactosidase or chloramphenicol transferase.

Construction of expression vectors containing the novel promoter sequences, such as the complete VDUP1 promoter sequence and its substantially similar complements, operably linked to DNA sequence encoding a polypeptide or nucleic acid product and capable of expressing said nucleic acid sequence product when transfected into a target host cell can be accomplished by methods known to one of skill in the art. Typically the VDUP1 promoter sequences and the DNA/RNA sequence encoding the desired product will be cloned into an expression vector via suitable restriction endonuclease sites such that the promoter is upstream of and in direct orientation with the DNA sequence. The expression vector may be a plasmid, virus or a cosmid, for example. The cloned expression vector may then be transfected into the target host cells and successfully transformed cells may be selected based on the presence of a suitable marker nucleic acid sequence as described above.

Generally, in addition to the heterologous nucleic acid sequence operably linked to the VDUP1 promoter sequences of this invention, the vector will contain at least one eukaryotic marker nucleic acid sequence, the appropriate eukaryotic transcriptional and translational stop signals, at least one Shine-Delgamo sequence and initiator codon, a signal that signals polyadenylation of the transcribed mRNA, and any other DNA sequences necessary or preferred for the appropriate transcription and translation of the heterologous DNA. These additional sequences may include a signal sequence for proteins to be exported or secreted from the host cell and at least one nucleic acid sequence for a transcriptional regulator protein. If the vector is used as an extrachromosomal replicating DNA in the eukaryotic cell where it is expressed, the vector will include an origin of replication that functions in the host cell. When the vector is to be integrated into the host chromosomal DNA, it will contain elements necessary to facilitate its integration into the host genome. These elements may be provided by viral vectors such as vaccinia and adenovirus, or by nonviral recombinant plasmids.

DNA is commonly transferred or introduced into recipient mammal cells by calcium phosphate-mediated gene transfer, electroporation, lipofection, viral infection and the like. General methods, vectors and general considerations for gene transfer and expression may be found in M. Kriegler, Gene Transfer and Expression: A Laboratory Manual, Stockton Press (1990). Direct gene transfer to cells in vivo is achieved by the use of modified viral vectors, including retroviruses, adenoviruses, adeno-associated viruses and herpes viruses, liposomes, and direct injection of DNA into certain cell types. In this manner, recombinant expression vectors and recombinant cells containing the novel VDUP1 promoters of the present invention operably linked to desired heterologous nucleic acid sequence can be delivered to specific target cells in vivo. See, e.g., Wilson, Nature, 365: 691–692 (1993); Plautz et al, Annals NY Acad. Sci., 716: 144–153 (1994); Farhood et al, Annals NY Acad. Sci., 716: 23–34 (1994) and Hyde et al Nature, 362: 250–255(1993). Furthermore, cells may be transformed ex vivo selected as described earlier and introduced directly at localized sites by injection, e.g., intra-articular, intracutaneous, intramuscular and the like.

Host cells provided by this invention expressing heterologous sequences under the control of the VDUP1 promoter sequences of this invention can be used to produce proteins, preferably human proteins and fragments thereof. The process involves culturing the transformed cell under conditions wherein the protein is expressed, optionally by inducing the activity of the promoter, and purifying the protein from the cell culture. Purification generally involves the steps of cell lysis, homogenization, centrifugation and separation of the desired protein by processes such as salt fractionation, precipitation, and a variety of chromatographic methods such as anion exchange chromatography, hydrophobic interaction chromatography, high resolution chromatography, gel filtration chromatography and the like.

Production of secreted recombinant or heterologous protein involves continuous culture of cells for a period typically of up to 14 days. In this process, cells seeded at approximately $10^5$ cells/ml double to a total density of 1–7 million cells/ml. At the point of cell saturation, the culture persists under stress conditions (eg: reduction in available nutrient components and an accumulation of metabolic by-products) for up to several days, at which point the culture eventually crashes with high mortality. During this period of maximal cell density and cell stress, the highest output of recombinant heterologous protein may be expected to occur.

The following examples are given to enable those of skill in the art to more clearly understand and practice the invention. They should not be considered as limiting the scope of the invention, but merely illustrative and representative thereof.

EXAMPLE 1
Identification and Characterization of the Mouse VDUP1 Promoter

Figure 2:
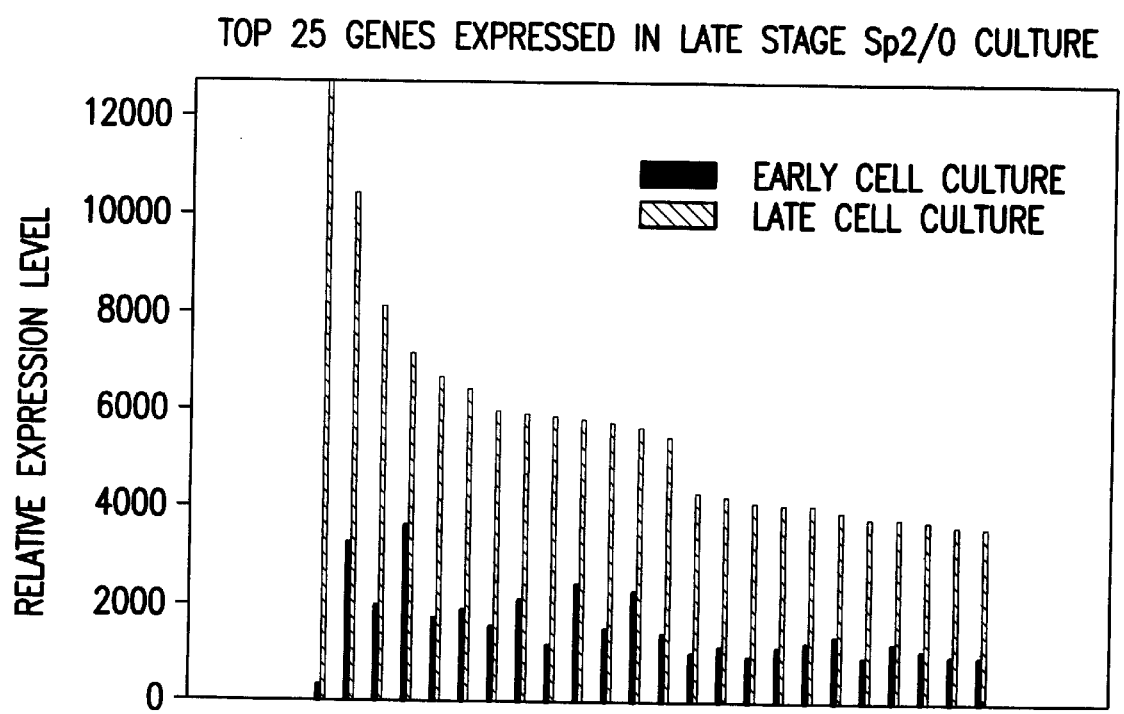
FIG. 2 is a graph showing the relative expression levels of the top 25 most expressed genes from a panel of 10,000 genes or Expressed Sequence Tags (ESTs) in the late stage relative to the early stage of an Sp2/0 cell culture. VDUP1 expression is represented by the data set out at the extreme left.

A representative RNA sample taken at a point early in the SP2/0 culture period (day 3), and a second sample late in the SP2/0 culture during the stationary phase of culture (day 8), were screened using differential gene array analysis to identify genes that were most strongly expressed in late SP2/0 culture. An array of approximately 10,000 mouse genes and uncharacterized ESTs were profiled for expression using the isolated early and late RNA samples. This analysis identified a large series of gene sequences, some unique and some previously characterized, exhibiting high level expression during late stage SP2/0 cell culture shown in FIG. 2. In many cases these genes were strongly up-regulated relative to the early culture period. Of those genes identified, an Expressed Sequence Tag (EST) with homology to the VDUP1 gene was recorded as most highly expressed and, particularly with respect to the early time point. According to differential gene array analysis, the VDUP1 gene was induced more than 18-fold between early and late time points. Furthermore, its relative expression level, as determined by RNA expression levels, was more then two-fold higher than the second most highly expressed candidate gene.

Subsequent investigation of VDUP1 gene expression in SP2/0 cells was carried out using Northern blot analysis, wherein mRNA from the isolates used for gene array screening was probed with a VDUP1 cDNA probe, alongside an internal ribosomal RNA gene probe control. The VDUP1 probe contained the full length DNA sequence of the murine VDUP1 open reading frame and was generated by polymerase chain reaction from a mouse embryonic day 15 cDNA library pool. The results indicated that the VDUP1 transcription was induced as much as 30-fold between early and late culture points.

Thus, two different assays for gene expression demonstrated that mouse VDUP1 represented a highly inducible gene in SP2/0 cells and was therefore a suitable gene for isolation and characterization of its promoter for eventual use in expression vector development.

EXAMPLE 2
Characterization of mouse VDUP1 regulation

Differential gene array analysis showed that the mouse VDUP1 gene was significantly up-regulated during prolonged cell culture. The identification and characterization of factors involved in the induction of VDUP1 in these systems required isolation of the functional promoter unit. In order to isolate the genomic DNA encoding the VDUP1 gene and its promoter, the full length cDNA probe was used to screen a mouse ('57/B6 genomic bacterial artificial chromosome library. Three clones were identified and one clone (7C21) was selected for mapping. Southern hybridization of restriction endonuclease digested BAC 7C21 was performed using a radiolabeled VDUP1 cDNA probe. The resulting band profile matched that observed from hybridization of this probe to digested mouse SP2/0 genomic DNA, confirming the presence of at least a portion of the VDUP1 gene within BAC 7C2 1. Subsequent hybridization using oligonucleotide probes specific for the 5' and 3' ends of the VDUP1 coding region confirmed that the entire VDUP1 coding region was present in BAC 7C21. Furthermore, these blots showed that considerable lengths of DNA sequence both upstream and downstream of the gene unit were present, suggesting that the entire VDUP1 gene was present within BAC 7C21. To isolate the 5' end of the VDUP1 gene containing the promoter region, restriction fragments detected by the 5' oligonucleotide probe were subcloned into pBluescript-II. A BamHI fragment of approximately 15 kb containing the 5' region and a portion of the VDUP1 coding region was isolated in this fashion. Subsequently, this fragment was further subcloned to a 3.0 kb EcoRI-BamHI fragment, containing approximately 2.8 kb of DNA sequence 5' to the VDUP1 ATG translational start. The proximal region of this subfragment was sequenced to 1448bp 5' to the ATG.

EXAMPLE 3
Promoter Sequence Analysis

Computational analysis of the VDUP1 5' upstream region identified multiple transcription factor binding sites. Many myeloid-specific elements were identified throughout the length of the region. Within the 597bp fragment (SEQ ID NO:3), sites for factors Sp1, CCAAT box, TATA box, and NF-κB were identified (FIG. 3). Furthermore, an octamer direct repeat sequence with homology to an upstream stimulation factor (USF/MLTF) element was also identified. This element contains a direct repeat of the core CACGAG spaced by 5 nucleotides. The consensus core for USF is CACGTG, although it has been shown to bind to a CAC-GAG sequence within the HLA-B promoter region. This element may be important in the inducibility of this promoter. In addition, NF-κB is a known stress inducible element and likely contributes to the induction of VDUP1 expression in prolonged cell culture. No consensus vitamin D3 response element (VDRE) was identified within the length of the 1448 bases (SEQ ID NO:1) of promoter region.

Primer extension mapping of the ends of VDUP1 mRNA was performed and 2 major start sites were identified. The most distal start site corresponded to a region approximately 20 nucleotides downstream from the TATA box at −278bp from the start codon. A second, stronger start site was further downstream, at −97. The length of the 5' ends of VDUP1 mRNA species suggests that the minimal functional promoter unit is significantly less than the 1448bp (SEQ ID NO:1) sequenced. (FIG. 3). The numbering for residue positions used above and elsewhere in the specification refers to the numbering used in SEQ ID NO:1 unless stated otherwise.

EXAMPLE 4
Deletion Constructs

Figure 4:
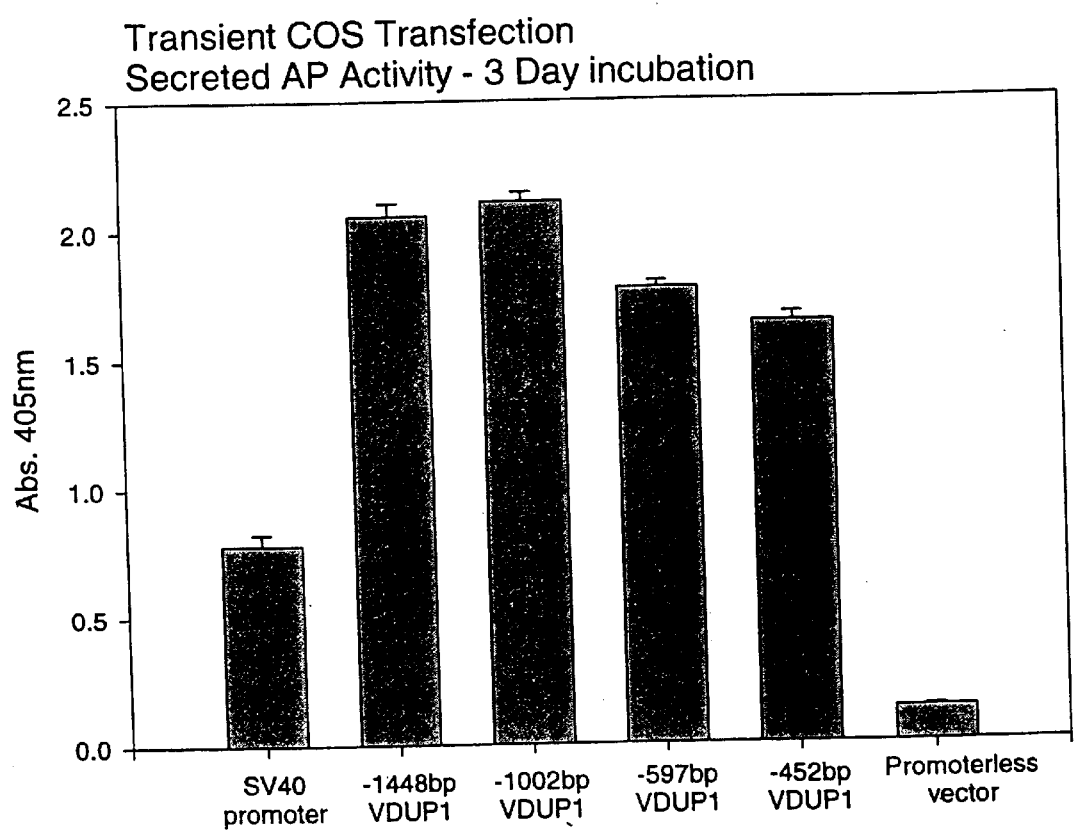
FIG. 4 is a graph showing secreted alkaline phosphatase (AP) activity upon transient transfection of COS cells of various VDUP1 promoter constructs operably linked to an alkaline phosphatase encoding nucleotide sequence.
Figure 5:
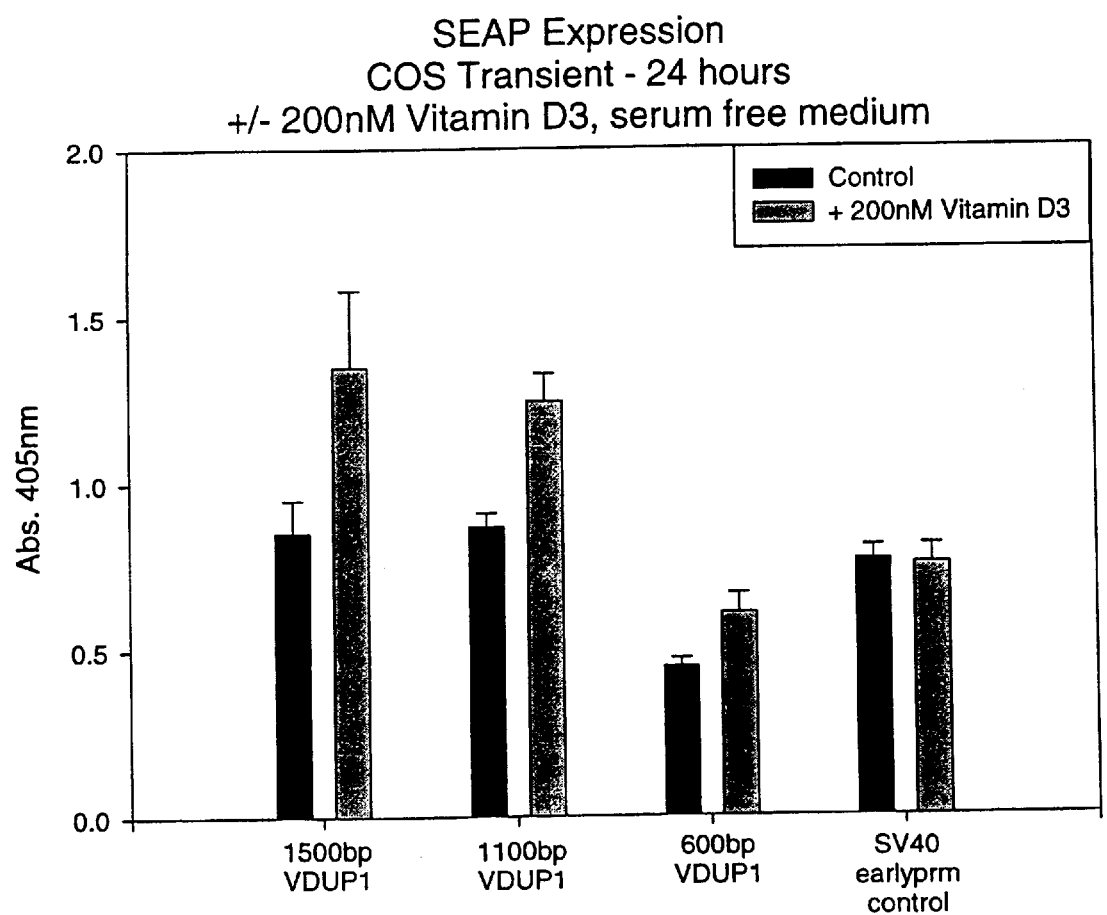
FIG. 5 is a graph showing secreted alkaline phosphatase (SEAP) activity upon transient transfection of COS cells of various VDUP1 promoter constructs operably linked to an alkaline phosphatase encoding nucleotide sequence, treated or untreated with 200 nM Vitamin D3.

Four deletion constructs were generated corresponding to 5' end lengths of 1448bp (SEQ ID NO:1), 1002bp (SEQ ID NO:4), 597bp (SEQ ID NO:3), and 452bp (SEQ ID NO:2) as shown in FIG. 1. In the 452bp (SEQ ID NO:2) construct, the two Sp1 elements are deleted. Each fragment was generated by PCR from the 3.0 kb EcoRI-BamHI subclone, and introduced upstream of the secreted alkaline phosphatase (AP) reporter nucleic acid sequence. Representative clones of each were verified by DNA sequencing. The VDUP1 constructs were then transfected into COS cells and screened for expression in comparison to an SV40 immediate early promoter driven AP construct. All four VDUP1 deletion constructs expressed the reporter nucleic acid sequence at similar levels, consistently higher than the SV40 control. At 6 days post transfection, VDUP1 promoter constructs expressed the reporter nucleic acid sequence at levels 2–2.5 times the SV40 control, suggesting some up-regulation of the promoter could be detected even in a transient transfection assay (FIG. 4). Treatment of transfected cells with 200 nM Vitamin D3 effected a 25% enhancement of VDUP1 expression in all constructs tested (FIG. 5). In contrast, the SV40 control was not induced by the addition of vitamin D3. Within the 452bp (SEQ ID NO:2) minimal promoter are the two transcriptional start sites, the TATA and CCAAT boxes, the USF/MLTF element, and the single NF-κB site. A functional expression vector utilizing the mouse VDUP1 promoter requires at minimum the sequences from −381bp, the site of the CCAAT box. Higher levels of expression were detected with the longer constructs. Thus, expression vectors will typically utilize the 1448bp (SEQ ID No:1)promoter. Longer promoter lengths can impart 'buffering' activity to an expression cassette suppressing fortuitous read-through transcription into the cassette.

EXAMPLE 5
VDUP1 Genomic Analysis

Figure 6:
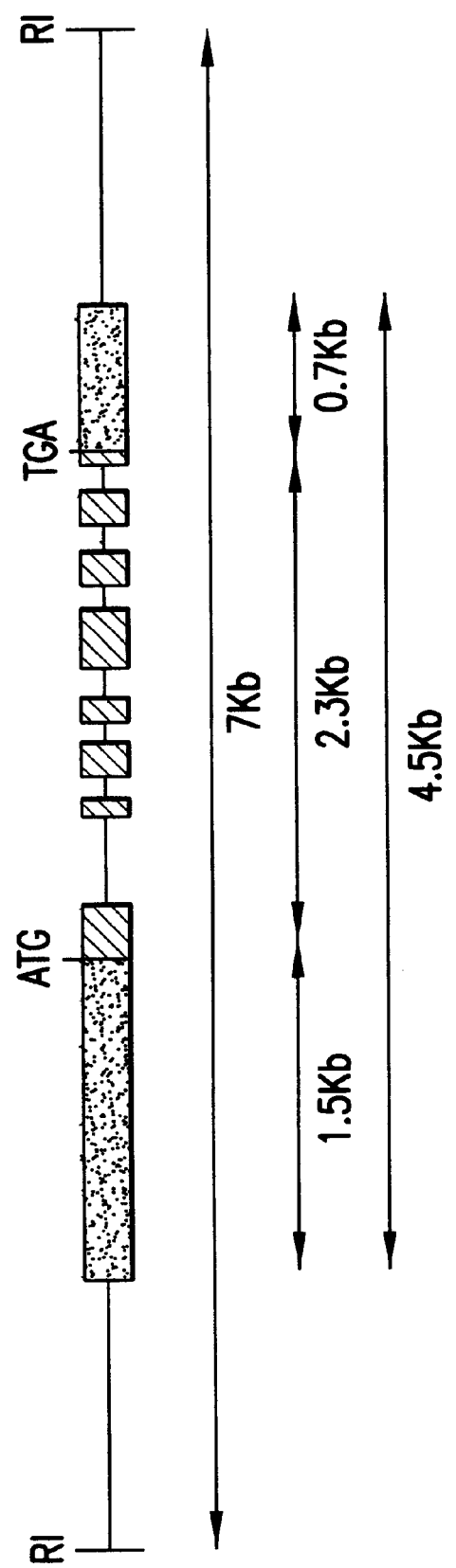
FIG. 6 is a schematic of the genetic map of the mouse VDUP1 gene showing the promoter region, start site, the 8 exons and 7 introns, the stop codon, and the 3' untranslated region.

The entire VDUP1 gene was cloned and sequenced. The gene is contained with approximately 5 kb of sequence, spaced between 8 exons (FIG. 6). The gene is located on mouse chromosome 3, band F2.2. This region is syntenic with human chromosome 1q21. The invention relates to any vectors generated containing the promoter region of VDUP1 and any transgenic animals generated by introduction of said vectors. This includes knockout animals to the locus or locus syntenic to human chromosome 1q21 or animals in which nucleic acid sequences are expressed from the endogenous VDUP1 promoter on human chromosome 3 or a mammalian chromosome syntenic to human chromosome 3. A fully functional expression cassette requires both a 5' promoter element and a 3' polyadenylation region. Maximal induction of the VDUP1 promoter may require the 1046bp untranslated region of the message's 3'end sequences.

EXAMPLE 6
Transgenic Animals

This invention also provides transgenic animals for expressing VDUP1 promoter operably linked heterologous protein, polypeptide, hormone, ribozyme, antisense messenger RNA and the like. Transgenic animals with genes comprising the VDUP1 promoters operably linked to a heterologous nucleic acid sequence can be prepared by methods known to those of skill in the art such as, but not limited to, B. Hogan et al, Manipulating the Mouse Embryo, Cold Spring Harbor Laboratory Press, New York (1986) and U.S. Pat. No. 5,162,215, R. A. Bosselman et al, Method of Gene Transfer into Chickens and other Avian Species (1992). Briefly, using mice as an example, fertilized eggs are collected by washing out the oviducts of mated females and a DNA construct of the VDUP1 promoter operably linked to a heterologous DNA sequence is microinjected into the pronuclei. The injected eggs are then transferred to and implanted in the uterus of foster mothers, female mice made pseudopregnant by mating with vasectomized males. After birth the progeny mice are checked for presence of the transgene by Southern blotting of DNA extracted from a small piece of the tail. If suitable primers are available, screening can be rapidly performed by polymerase chain reaction. The transgene may be integrated into the germ line cell, somatic cells or both. Transgenic mice carrying the transgene in their germ line cells can be identified by mating them with normal nontransgenic mice and determining whether the inheritance of the transgene follows expected Mendelian genetics. This is often conveniently accomplished by including in the injected DNA construct a nucleic acid sequence coding for readily visible trait such as skin coat color. An alternative method of transgenic animal production involves injecting a DNA construct comprising the novel VDUP1 promoters of this invention into undifferentiated embryonic stem cells prior to injecting into the mouse blastocyst. Such transgenic animals provide an animal model for production of heterologous protein, polypeptide, hormone, ribozyme, antisense messenger RNA and the like. High level induction of nucleic acid sequence expression of pharmacologically active proteins in transgenic animals allows one to study and identify therapeutically agents for the treatment of human disease in an animal model. The animals carrying nucleic acid sequences comprising the VDUP1 promoter sequences disclosed herein can be used to test for compounds which modulate gene expression in vivo, in particular by regulating the promoter activity of the VUDP1. Thus such transgenic animals may be used to identify compounds which reverse this upregulation.

Introduction of the desired DNA sequence at the fertilized oocyte stage ensures that the transgene is present in all of the germ cells and somatic cells of the transgenic animal and has the potential to be expressed in all such cells. The presence of the transgene in the germ cells of the transgenic "founder" animal means that all of its progeny will in turn carry the transgene in all of their germ line and somatic cells. Conversely, introduction of the transgene at a later embryonic stage in a founder animal may result in limited presence of the transgene in some somatic cell lineages of the founder animal. Chimeric animals in which fewer than all of the somatic and germ cells contain the transgenic DNA sequence of the present invention, produced for example, when fewer than all of the cells of the morula are transfected in the process of producing the transgenic animal are also within the scope of the present invention. Transgenic animals may also be used as bioreactors for the production of large amounts of a desired protein. Production of certain physiologically active proteins which require unique glycosylation patterns for correct folding and processing may require their expression in specific mammalian cells.

EXAMPLE 7
Assay for Test Agents that Regulate the VDUP1 Promoter

The invention also provides a method of screening for test compounds that regulate the activity of the VDUP1 promoter. This is accomplished by contacting a transformed host cell in which the VDUP1 promoter disclosed herein is operably linked to a reporter nucleic acid sequence with a test medium containing the test compound under conditions which allow for expression of the reporter nucleic acid sequence Candidate test agents are screened by measuring the expression of the reporter nucleic acid sequence in the presence of media containing the test agent, and comparing it under identical conditions, to reporter nucleic acid sequence activity in the presence of a control medium which does not contain the test compound but is otherwise identical to the test medium. Any difference in expression between the test agent containing media and control media is correlated to the ability of the test agent to regulate the activity of the VDUP1 promoter.

REFERENCES

Chen et al., "Isolation and characterization of a novel cDNA from HL-60 cells treated with 1,25-dihydroxyvitamin D-3". Biochem. Biophys. Acta 1994 Sep 13;1219(1) :26–32

Yang et al., "Expression of a vitamin D-regulated gene (VDUP-1) in untreated- and MNU-treated rat mammary tissue." Breast Cancer Res. Treat. 1998 Mar;48(1):33–44.

Nishiyama et al., "Identification of thioredoxin-binding protein-2/vitamin D(3) up-regulated protein 1 as a negative regulator of thioredoxin function and expression." J. Biol. Chem. 1999 Jul 30;274(31):21645–50.

Young et al., "Alteration of gene expression in rat mammary tumors induced by N-methyl-N-nitrosourea." Mol. Carcinog. 1996 Apr; 15(4):251–60.

What is claimed is:

1. A substantially purified nucleic acid molecule comprising a VDUP1 promoter region, whose expression is induced to maximal levels as a result of prolonged cell culture, having a sequence consisting of a nucleic acid sequence hybridizing under high stringency conditions to that of SEQ ID NO:1, which exhibits promoter activity.

2. The nucleic acid molecule of claim 1, wherein said nucleic acid molecule comprises a CCAAT box, TATA box, NF-kB binding site, Sp1 binding site, and an octamer direct repeat sequence substantially similar to an upstream stimulation factor (USF/MLTF) element.

3. Then nucleic acid of claim 2, wherein said upstream stimulation factor (USF/MLTF) element comprises a direct repeat of the core CACGAG spanned by five nucleotides.

4. A substantially purified nucleic acid molecule comprising a VDUP1 promoter region, whose expression is induced to maximal levels as a result of prolonged cell culture, having a sequence consisting of a nucleic acid sequence hybridizing under high stringency conditions to that of SEQ ID NO:2, which exhibits promoter activity.

5. The nucleic acid molecule of claim 4, wherein said nucleic acid molecule comprises a CCAAT box, TATA box, NF-kB binding site, an octamer direct repeat substantially similar to an upstream stimulation factor (USF/MLTF).

6. The nucleic acid of claim 5, wherein said upstream stimulation factor (USF/MLTF) comprises a direct repeat of the core CACGAG spanned by five nucleotides.

7. An expression vector comprising the nucleic acid molecule of claim 1 or 4.

8. The vector of claim 7, wherein the nucleic acid molecule is operably linked to a heterologous nucleic acid sequence.

9. The vector of claim 8, wherein said heterologous sequence is a reporter sequence.

10. The vector of claim 9, wherein said reporter sequence encodes alkaline phosphatase.

11. The vector of claim 8, wherein said heterologous sequence encodes an immunoglobulin subunit.

12. The vector of claim 11 wherein said heterologous sequence encodes immunoglobulin light and/or heavy chains.

13. A host cell transformed with the vector of claim 8.

14. The host cell of claim 13, wherein said host cell is a eukaryotic cell.

15. The host cell of claim 14, wherein said host cell is a mammalian cell.

16. The host cell of claim 15, wherein said host cell is a COS cell.

17. The host cell of claim 15, wherein said host cell is a human cell.

18. The host cell of claim 17, wherein said host cell is from a HL-60 cell line.

19. The host cell of claim 17, wherein said host cell is from a 293 production cell line.

20. The host cell of claim 15, wherein said host cell is a murine cell.

21. The host cell of claim 20, wherein said host cell is from a mouse myeloma SP2/0 cell line.

22. The host cell of claim 20, wherein said host cell is from a mouse NSO cell line.

23. An expression vector comprising a VDUP1 promoter region, whose expression is induced to maximal levels as a result of prolonged cell culture; having a sequence consisting of a nucleic acid sequence hybridizing under high stringency conditions to that of SEQ ID NO:1, which exhibits promoter activity.

24. A method for producing a nucleic acid sequence product comprising culturing the host cells of claim 13 under conditions wherein said nucleic acid sequence product is produced and recovering the nucleic acid sequence product from the cell culture.

25. The method of claim 24, wherein said host cell is a COS cell.

* * * * *